Figure 1:
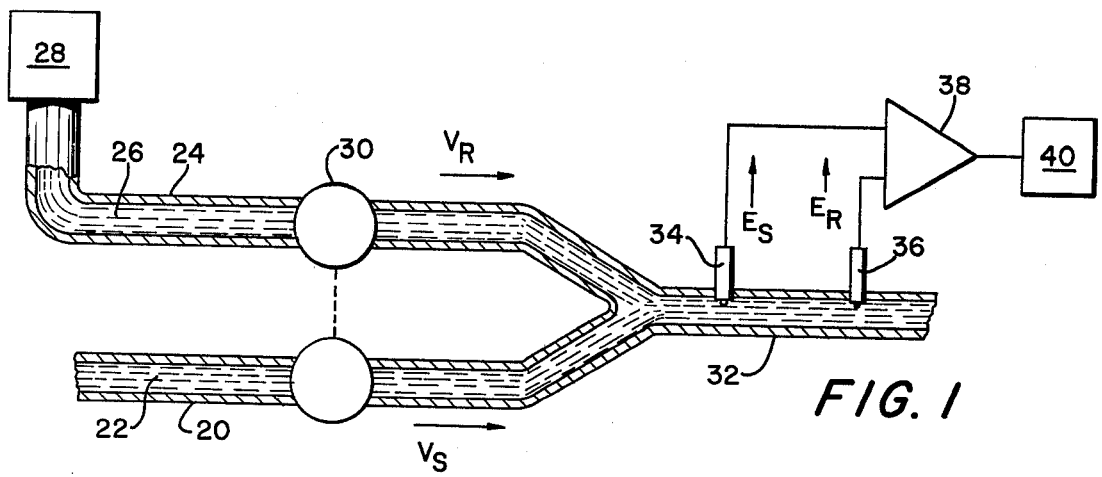

United States Patent [19]
Riseman et al.

[11] 3,964,988
[45] June 22, 1976

[54] ELECTROCHEMICAL MONITORING

[75] Inventors: John H. Riseman, Cambridge; Martin Frant, Newton, both of Mass.

[73] Assignee: Orion Research Incorporated, Cambridge, Mass.

[22] Filed: Jan. 19, 1972

[21] Appl. No.: 218,881

[52] U.S. Cl............................................ 204/195 M
[51] Int. Cl.²..................................... G01N 27/46
[58] Field of Search........ 204/195 M, 195 G, 195 R, 204/195 F

[56] References Cited
UNITED STATES PATENTS

| | | | |
|---|---|---|---|
| 3,306,837 | 2/1967 | Riseman et al. | 204/195 G |
| 3,556,950 | 1/1971 | Dahms | 204/195 R |

FOREIGN PATENTS OR APPLICATIONS

| | | | |
|---|---|---|---|
| 271,717 | 11/1961 | Netherlands | 204/195 G |

OTHER PUBLICATIONS

Jacobson, "Anal. Chem., " vol. 38, No. 13, Dec. 1966, pp. 1951-1954.

Monahan, "Anal. Chem.," vol. 42, No. 1, 1970, Jan., pp. 128 & 129.

*Primary Examiner*—T. Tung
*Attorney, Agent, or Firm*—Schiller & Pandiscio

[57] ABSTRACT

A system for electrochemical monitoring for the appearance of an ionic species of interest in a first flow stream by merging the first flow stream with a second flow stream containing a mixture of the ion to be sensed and a second non-interfering tag ion in a substantially fixed ratio. A pair of ion-sensing electrodes responsive, respectively, to the ionic species of interest and the tag ion are used to detect the activity of the species at a location in the merged stream. The difference between the measured potentials of the two ionic species in the merged stream is a constant ratio which is unaffected by fluctuations in the rate at which the two flow streams are mixed.

6 Claims, 2 Drawing Figures

ELECTROCHEMICAL MONITORING

This invention relates to electro-chemical analytical systems, and more particularly to alarm systems for substantially continuously monitoring of fluid streams for the possible appearance of selected ionic constituents with ion-sensitive electrodes.

Various continuous monitoring or sensing systems using ion-sensitive electrodes are known in the art for providing information relating to the activity of an ionic species of interest, or to the concentration thereof. Such systems generally comprise a reference electrode and an electrode sensitive to the ion of interest. The reference and ion-sensitive electrodes typically provide an electrical signal which is a function of the logarithmn of the activity in the stream of the ionic species to which the electrode is sensitive, i.e., exhibit a response which is substantially according to the well-known Nernst equation. A large number of such electrodes are known and described in detail in the literature, as for example in R. A. Durst "Ion-Sensitive Electrodes", National Bureau of Standards, special publication 134, (1969).

In some cases, however, there may normally be none of the ion of interest present, and the information desired relates then to monitoring the system for the possible appearance of the ion of interest. Such information, for example, would be used to detect leaks into boiler or cooler systems, or to detect failure or saturation of an ion exchange column.

When one employs an ion-sensitive electrode to monitor a solution where normally none of the ion of interest is present in the solution, the electrode tends to provide spurious potentials due to interferences, or it drifts widely with time. In order to overcome this problem, it has been proposed to introduce a low level of the ion which is being sensed, as a continuous background by techniques known variously as "spiking" or "standard addition." The level of background ion added by such process has to be sufficiently low so that any increase in the concentration of that ion, due to example, to leakage or other cause, will immediately trigger the alarm system. However, if the flow rate of background reagent being introduced varies, the alarm system may be triggered. In practice, it is very difficult to maintain a constant and exact flow rate of background ion reagent. For example, even with a peristaltic proportioning pump, tubing may vary in elasticity and diameter, back pressure due to head varies as the reagent is consumed, reagent viscosity may change or the reagent may vary in temperature (and hence viscosity and density). With conventional check valve type pumps, leakage around the piston and check valves may develop in the reagent channel. These problems are particularly severe in monitoring alarm systems which operate with relatively small volumes and low flow rates and low ion levels.

A principal object of the present invention is to provide a system for monitoring with ion-sensitive electrodes, which system is basically unaffected by fluctuations of pumping rates, and wherein the output is independent of variations in the flow rate of the reagent stream. Generally, this object is effected by adding to the sample stream a reagent stream containing a substantially fixed ratio of both the ion to be sensed and a suitable non-interfering or tag ion, and sensing the difference in potential between an electrode responsive to the ion of interest and an electrode responsive to the tag ion, both electrodes being placed in the mixed stream. This system has the unique advantage of being effectively independent of the rate of reagent addition to the sample stream.

The term "flow rate" as used herein is intended to mean the volume of liquid passing a given point per unit of time.

Other objects of the invention will in part be obvious and will in part appear hereinafter. The invention accordingly comprises the apparatus possessing the construction, combination of elements, and arrangement of parts, and the process including the several steps and the relation of one or more of such steps with respect to each of the other, all of which are exemplified in the following detailed disclosure and the scope of the application of which will be indicated in the claims.

Figure 2:
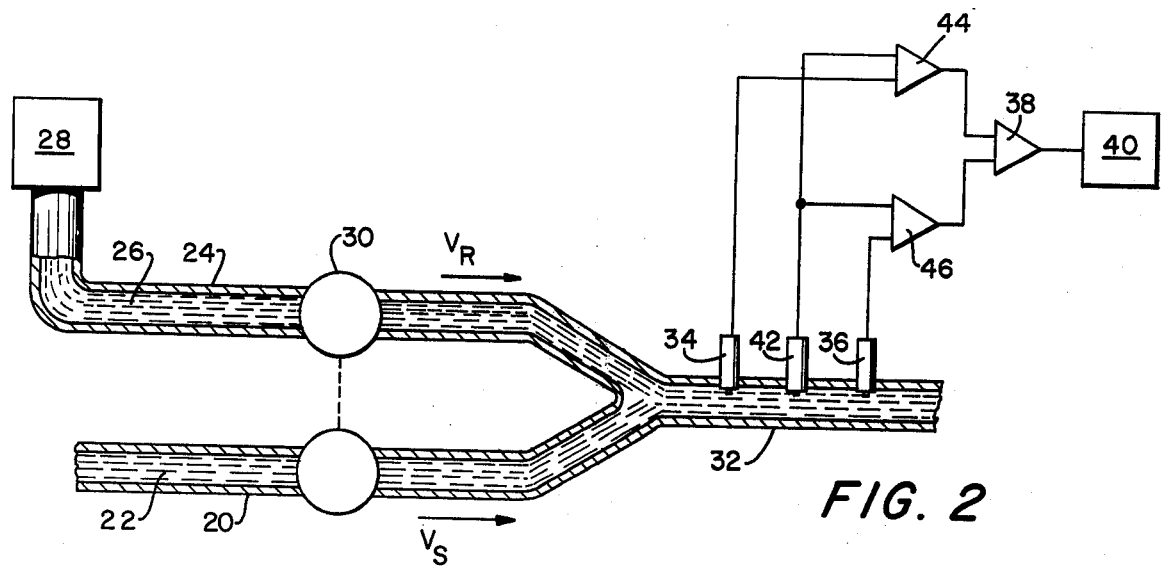

For a fuller understanding of the nature and objects of the present invention, reference should be had to the following detailed description taken in connection with the accompanying drawings wherein FIG. 1 shows a preferred embodiment of the present invention, partly in cross-section and partly schematically; and FIG. 2 shows a schematic diagram of an alternative embodiment of the present invention.

In the embodiment of FIG. 1 there is shown a first conduit 20 for conveying a stream of fluid 22 which is being monitored for the possible presence of an ion of interest, and a second conduit 24 which is intended to convey a stream of fluid 26 containing a reagent or liquid having therein a mixture of a small amount of the ions of interest, and a non-interfering or tag ion. Reagent 26 is supplied from reservoir 28. The supply of sample fluid 22 is not shown but obviously can be obtained from any source, such as the effluent from an ion exchange column, which is to be monitored for the possible presence of an ion of interest.

The device includes pump means 30, in its preferred form, shown as a dual pump, capable of delivering an output of reagent and sample streams at pumped flow rates indicated respectively as $V_R$ and $V_S$. Alternatively, pump means 30 can be two separate pumps. Pumping should be arranged to use as little reagent as practicable, typically in the order of one or two ml/minute. As an alternative embodiment, one or both of the sample and reagent streams may be gravity fed. Pump means 30 are disposed to pump the liquids in conduits 20 and 24 into a common conduit 32 wherein reagent stream 26 and sample stream 22 are intimately mixed. The electrodes most useful in the present invention are generally those which provide an electrical signal which is a function of the logarithm of the activity in the stream of the ionic species to which the electrode is sensitive, i.e., exhibit a response which is substantially according to the well-known Nernst equation. The device therefore includes two such electrodes, 34 and 36, the former being sensitive to the ionic species of interest and the latter being sensitive to a second ionic species to which electrode 34 is non-responsive. Similarly, electrode 36 should be non-responsive to the ionic species of interest. Both electrodes are disposed so as to be in contact with the mixed stream in conduit 32.

The output of each electrode 34 and 36 is connected to respective inputs of differential amplifier 38 of appropriate input impedence. Amplifier 38 may have variable gain if desired.

In operation, electrode 34 responds to the activity of the sample ion S+ in the mixed stream in conduit 32 to provide output signal $E_S$ substantially according to the equation:

$$E_S = E° + (RT/F) \log S^+ \qquad (1)$$

where E° is a constant potential, RT/F is the well-known constant slope in accordance with the Nernst equation, and S+ is the activity of the sample ion. In like manner, electrode 36 in mixed stream 32 responds to the activity of the tag ion R in the mixed stream to provide an output signal $E_R$ substantially according to the equation:

$$E_R = E° + (RT/F) \log R^+ \qquad (2)$$

where E° and RT/F are as defined above, and R+ is the activity of the tag ion.

The difference between the outputs of the two electrodes is read as the output Eo of differential amplifier 38 according to the equation:

$$Eo = E_S - E_R = (RT/F) \log (S^+/R^+) \qquad (3)$$

Thus the electrode pair responds to the ratio of the activities of the two ions which are present in the mixed stream 32. Given the situation where no ion species of interst(s) is in the sample stream 22, the mixed stream in conduit 32 will comprise the sample and ions S and R in a constant ratio, because at least some reagent stream 26 is present. Since reagent stream 26 is then the only source of ions S and R, the response of the electrodes will be unaffected by fluctuations in the rate at which reagent stream 26 is mixed with sample stream 22.

However, given the appearance of some ion species S of interest in sample stream 22, the ratio of the two ions in mixed stream 32 will be affected, and the output of differential amplifier 38 will change. Thus by attaching readout device 40 to the output of differential amplifier 38 in the form of a direct reading meter scale, or as appropriate circuitry connected to the output of amplifier 38 to cause an alarm to trigger, a monitoring system which detects the presence of a selected ion in a sample stream is provided.

The tag ion R in stream 26 preferably should have the same charge and valence as the ion S to be sensed. For example, if the sample ion is a monovalent cation, the tag ion should only be a monovalent anion, e.g. I– and F–.

However, one can still employ a wide variety of tag or reagent ions and still achieve the desired fixed ratio through the electronics employed. For example, if the tag ion has the same valence as the sample ion but is of different charge (e.g. tag ion is F– and sample ion is Na+) then as shown in FIG. 2, the invention includes an electrical reference electrode 42, and a pair of preamplifiers 44 and 46. Preamplifier 44 has its inputs connected to electrodes 34 and 42 so that the latter constitutes a reference or base level for the signal from electrode 34. Similarly, preamplifier 46 has its inputs connected to electrodes 36 and 42 so that the output of the latter is the reference level for $E_R$ from electrode 36. Reference electrode 42 can be any of a large number of known stable reference electrodes, typically Ag/AgCl electrode, or the like.

One of the amplifiers 44 and 46 inverts its output while the other of these amplifiers is non-inverting. The outputs of preamplifiers 44 and 46 are connected to the inputs of differential amplifier 38.

One can also employ a tag ion with a sample ion of the same charge but with different valence (e.g. Ag+ and Ca++) in which case the preamplifiers are both inverting or non-inverting as the case may be, and the gain on the silver electrode preamplifier is set to double the gain of the calcium electrode preamplifier.

While generally, one can use any of a large number of pairs of ion-sensing electrodes to achieve a fixed ratio (provided that the correct gains and senses are used in the respective electrode preamplifiers), the need for reference electrode 42 can only be eliminated by employing as electrodes 34 and 36, a pair which respond to different ions of the same valence and charge.

As noted the reagent contains tag and sensed ions in some predetermined, fixed proportion or ratio. In determining this ratio, it should be noted that the levels of tag ion R and sensed ion S added to conduit 32 by stream 26 have to be high enough to achieve stability and an adequate equilibrium at the electrode interface. On the upper side, the tag ion can be added at a level anywhere up to a saturated solution. It is believed that the lower limit is set by the electrode characteristics. The lower limit of detection for most specific ion electrodes is determined by the small but finite solubility of the sensing element in the electrode. Since the sensing element usually contains a species to which the electrode responds, the electrode "interferes" with itself in dilute solutions. Theoretically, the absolute lower limit of detection is thus a function of the smallest increase in electrode potential which unequivocally indicates the presence of the ion being sensed. However, since electrode potentials are not very stable at or near zero concentration of the ion of interest and they tend to drift and to respond to interferences, it is difficult to obtain a reproduceable value for the absolute limit. Therefore, for the lower limit, it is preferred to add at least that level of ion which is equal to or greater than the so-called "mud level" which is the apparent concentration of a zero concentration solution, as read from an extrapolation of the Nernst calibration curve. Details of the "mud level" are described in the literature, as for example, in the article "Mud and Water," Orion Newsletter, January/February (1971).

The background level of sensed ion S added in the reagent stream has to be high enough to give stability at the electrode interface, but it has to be sufficiently low so that an increase of that ion in the sample stream will have a measurable effect on the overall ratio of the tag ion to the sample ion. This means that the level of added sample ion is related to the minimum quantity of sample ion to be detected in the sample stream. From a practical standpoint the upper limit of intentionally added sample ion is considered to be about four times the amount of ion which it is desired to sense. Since the art has reported error of a factor of about two at reading at the so-called "mud level," the lower limit of added sample ion is considered to be a minimum value of about twice the apparent "mud level," at which level reproduceable results can be obtained. It should be noted that the choice of added sample ion level makes it possible to vary the threshold level of detection. In some instances, such as when monitoring ion-exchange column "breakthrough," this may be a desirable feature.

The reagent stream and the sample stream can be added in any ratio provided the levels of ions added are within the above-mentioned preferred ranges. However, as the quantity of ions in the reagent stream 26 increases compared to the quantity of ions in sample stream 22, the ability to detect small amounts of ion S in the sample stream decreases. Accordingly, it is preferred to add the ions of the reagent stream at a rate which is at most between 10 and 50 times the rate of addition of the sample stream. At the lower end, it is desirable to keep the rate of reagent stream addition small relative to the rate of sample stream addition. On a practical basis a preferred lower limit for the relative rate of addition of the reagent stream is not less than about 1/1000 the rate of sample stream addition.

The following examples are illustrative of the monitoring systems which can be achieved by the present invention.

EXAMPLE I

In order to show the magnitude of electrode drift in a stream of relatively pure water, a monitoring system for fluoride was built as follows:

An aqueous sample stream comprising substantially pure water was taken up from a sample pool of distilled and deionized water through a 1/16 inside diameter Tygon (plasticized polyvinyl chloride) tubing, and passed through one channel of 4-channel peristaltic pump.

A separate channel of the same pump drew a reagent stream comprising an aqueous solution of $2.5 \times 10^{-3}$ M sodium iodide, $2.5 \times 10^{-3}$ M acetate/acetic acid pH buffer and 1 g/l of a complexing agent for aluminum, (CDTA). This reagent stream was mingled in a single conduit with the sample stream in a 1:1 ratio by the pump. The reagent here was intended to fix the ionic stength of the water at a uniformly measurable level, adjust the pH, and free any fluoride in the sample stream from complexing agents. However, it should be noted that the reagent contained no fluorides. The mingled solution was then directed through a mixing chamber, which was formed of a small cylindrical section containing a magnetic stirrer, and thence into an electrode chamber. The electrode chamber contained two electrodes, a fluoride-sensng electrode, and an iodide-sensing electrode (respectively Model Nos. 94-09 and 94-53 available commercially from Orion Research Incorporated, Cambridge, Mass.). From the electrode chamber, the mixed stream went to waste. Each electrode was connected to an electronic circuit serving as a differential amplifier and readout.

The system was started up at a flow rate of about 1 ml/min. After about 15 minutes a bucking or bias potential was applied and the difference between the electrode pair was arbitrarily set to read +44.5 mv. Over a period of 24 hours the potential difference between the electrode pair was observed to vary about 20 to 30 millivolts.

The observed drifty behavior was ascribed principally to two causes. First the fluoride sensitive electrode tended to respond to the fluoride level which was established by dissolution of its own ion-sensitive material, lanthanum fluoride. Since this was strongly affected by stirring rate and local variation in flow pattern, the electrode potential tended to wander. Secondly, since the fluoride concentration was many orders of magnitude from the isopotential point (concentration at which temperature effects are minimal), any small change in temperature tended to exaggerate the changes in electrode potential caused by dissolution of the membrane material as well as changing the solubility of the membrane material.

EXAMPLE II

The same physical arrangement was used as in the preceeding example, except that the reagent stream included $10^{-4}$ M (1.9 ppm) sodium fluoride. Both channels were fed this reagent stream.

After an initial 15 minutes of operation, a bucking or bias potential was applied and the difference between the electrode pair was again arbitrarily set to read +44.5 mv. Over a period of 24 hours, the potential difference between the electrode pair was observed to vary by less than about 0.3 mv. The constant addition of fluoride ions in the reagent stream insured that at least some fluoride ion was always present in the mixed stream. After 24 hours, one of the inputs was replaced with an input of pure distilled and deionized water, which was equivalent to changing the rate of reagent addition by 50%. Notwithstanding such 50% variation in the rate of reagent addition, the potential difference between the electrode pair was observed to shift only from +44.3 mv. to +44.0 mv.

The system was run for another 45 minutes during which time the electrode potential was observed to be stable to within 0.2 mv. Thereafter, the pure water input was replaced by an aqueous input containing (1 ppm) of fluoride. The difference in potential between the two electrodes was observed after about five minutes and was found to have shifted from +44.0 mv to +32.0 mv. This is in excellent agreement with theory which predicts a change of 11.8 mv. Over a period of 15 minutes, the potential difference between the electrode pair was observed to vary about 0.2 mv. The 1 ppm fluoride solution input was then replaced with pure distilled and deionized water input. After about five minutes, the potential difference between the electrode pair was observed to read +43.5 mv. for about 15 minutes after which the difference in potential was observed to gradually drift to about +44.0 mv. over the next 90 minutes.

It should be noted that the procedure of the present invention has unique advantages. First, the system is extremely stable when there is no ion of interest present in the sample stream. Secondly, even gross variations in the rate of reagent addition have virtually no effect on the electrode reading. Thirdly, the system responds quickly and in a substantially theoretical manner when a small amount of the ion of interest appears in the sample.

Since certain changes may be made in the above apparatus and made without departing from the scope of the invention herein involved it is intended that all matter contained in the above description or shown in the accompanying drawing shall be interpreted as illustrative and not in a limiting sense.

What is claimed is:

1. Apparatus for electrochemical monitoring of a first liquid flow stream for the presence of an ionic species of interest comprising in combination;
    a second liquid flow stream containing the ion species of interest and a second non-interfering ion species in a substantially fixed ratio to one another;
    means for combining said first and second flow streams to provide a mixed liquid;
    one electrochemical electrode for providing an electrical signal as a function of the activity of said ionic species of interest in said mixed liquid;

another electrochemical electrode for providing an electrical signal as a function of the activity of said second species of ion in said mixed liquid;

both of said electrodes being disposed in operative contact with said mixed liquid; and means for determining a difference signal between the electrical signals from said electrodes.

2. Apparatus as defined in claim 1 including pump means for providing said first and second flow streams at an approximately fixed ratio of flow.

3. Apparatus as defined in claim 1 including means for inverting one of said electrical signals before determining said difference signal.

4. Apparatus as defined in claim 1 including means for amplifying one of said electrical signals by a factor proportional to the ratio of the ionic charges of said species before determining said difference signal.

5. Apparatus as defined in claim 1 wherein said means for combining comprises first and second conduits for conveying said first and second flow streams respectively, and meeting at a junction, and a third conduit for conveying the mixed flow streams from said junction, said electrodes being emplaced in said third conduit.

6. Apparatus as defined in claim 1 including means responsive to any change in said difference signal.

* * * * *